United States Patent
Bingham et al.

(10) Patent No.: US 10,405,545 B2
(45) Date of Patent: Sep. 10, 2019

(54) COMPOSITIONS AND METHODS HAVING IMPROVED EFFICACY AGAINST SPORES AND OTHER ORGANISMS

(71) Applicant: GOJO Industries, Inc., Akron, OH (US)

(72) Inventors: James Edmund Bingham, Akron, OH (US); Christopher M. Fricker, Copley, OH (US); Michael J. Dolan, Akron, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 15/947,362

(22) Filed: Apr. 6, 2018

(65) Prior Publication Data

US 2018/0220647 A1    Aug. 9, 2018

Related U.S. Application Data

(63) Continuation of application No. 15/411,286, filed on Jan. 20, 2017, now Pat. No. 9,936,695, which is a continuation of application No. 14/615,691, filed on Feb. 6, 2015, now Pat. No. 9,578,879.

(60) Provisional application No. 61/937,060, filed on Feb. 7, 2014.

(51) Int. Cl.
| | |
|---|---|
| *A01N 37/16* | (2006.01) |
| *A01N 31/02* | (2006.01) |
| *A01N 37/12* | (2006.01) |
| *A61L 2/16* | (2006.01) |

(52) U.S. Cl.
CPC ............. *A01N 37/16* (2013.01); *A01N 31/02* (2013.01); *A01N 37/12* (2013.01); *A61L 2/16* (2013.01)

(58) Field of Classification Search
CPC ........ A01N 37/16; A01N 31/02; A01N 37/12; A61L 2/16
USPC ......................................................... 514/557
See application file for complete search history.

(56) References Cited

U.S. PATENT DOCUMENTS

| | | |
|---|---|---|
| 3,169,986 A | 2/1965 | Webb et al. |
| 3,829,468 A | 8/1974 | Serad et al. |
| 3,968,248 A | 7/1976 | Boucher |
| 3,978,032 A | 8/1976 | Manner |
| 3,983,252 A | 9/1976 | Buchalter |
| 4,004,977 A | 1/1977 | Kato et al. |
| 4,008,175 A | 2/1977 | Barter |
| 4,051,058 A | 9/1977 | Bowing et al. |
| 4,051,059 A | 9/1977 | Bowing et al. |
| 4,518,585 A | 5/1985 | Greene et al. |
| 4,557,898 A | 12/1985 | Greene et al. |
| 4,691,043 A | 9/1987 | Demame et al. |
| 4,900,721 A | 2/1990 | Bansemir et al. |
| 4,927,638 A | 5/1990 | Bykadi et al. |
| 4,946,868 A | 8/1990 | Demame et al. |
| 4,956,170 A | 9/1990 | Lee |
| 4,983,635 A | 1/1991 | Martin |
| 5,062,979 A | 11/1991 | Scharf et al. |
| 5,200,189 A | 4/1993 | Oakes et al. |
| 5,200,198 A | 4/1993 | Geisslinger et al. |
| 5,219,887 A | 6/1993 | Andrews et al. |
| 5,236,614 A | 8/1993 | Jacquet et al. |
| 5,284,875 A | 2/1994 | Martin |
| 5,314,687 A | 5/1994 | Oakes et al. |
| 5,322,856 A | 6/1994 | Martin |
| 5,378,731 A | 1/1995 | Andrews et al. |
| 5,380,756 A | 1/1995 | Andrews et al. |
| 5,436,008 A | 7/1995 | Richter et al. |
| 5,437,868 A | 8/1995 | Oakes et al. |
| 5,489,434 A | 2/1996 | Oakes et al. |
| 5,490,980 A | 2/1996 | Richardson et al. |
| 5,492,932 A | 2/1996 | Kundsin |
| 5,569,691 A | 10/1996 | Guggenberger et al. |
| 5,597,791 A | 1/1997 | Richards et al. |
| 5,620,655 A | 4/1997 | Nevermann |
| 5,631,218 A | 5/1997 | Allan et al. |
| 5,718,910 A | 2/1998 | Oakes et al. |
| 5,728,404 A | 3/1998 | von Rheinbaben et al. |
| 5,749,924 A | 5/1998 | Murch et al. |
| 5,767,054 A | 6/1998 | Sprugel et al. |
| 5,767,163 A | 6/1998 | Kundsin |
| 5,783,146 A | 7/1998 | Williams, Jr. |
| 5,800,827 A | 9/1998 | Igarashi et al. |
| 5,830,488 A | 11/1998 | Suzuki et al. |

(Continued)

FOREIGN PATENT DOCUMENTS

| | | |
|---|---|---|
| EP | 320219 | 6/1989 |
| GB | 1539771 | 2/1979 |
| WO | 9113058 | 9/1991 |
| WO | 9301716 | 4/1993 |
| WO | 2006093792 | 8/2006 |
| WO | 2006096148 | 9/2006 |
| WO | 2007018923 | 2/2007 |
| WO | 2009050447 | 4/2009 |
| WO | 2010035008 | 4/2010 |
| WO | 2010059531 | 5/2010 |
| WO | 2010127231 | 11/2010 |

OTHER PUBLICATIONS

McDonnell, Gerald et al., "Antiseptics and Disinfectants: Activity, Action, and Resistance", Clinical Microbiology Reviews, vol. 12, pp. 147-179 (Jan. 1999).

(Continued)

*Primary Examiner* — Kristin A Vajda
(74) *Attorney, Agent, or Firm* — Calfee, Halter & Griswold LLP (57) ABSTRACT

Compositions and methods for the disinfection of surfaces are provided. The compositions include an alcohol and a peracid. The disinfectant composition is characterized by a pH of no more than about 5. Broad spectrum efficacy is achieved, and synergistic activity is exhibited against bacterial and fungal spores, including *Clostridium difficile* spores. The compositions and methods are also useful against conformationally altered prions, bacteria, fungi, and viruses.

12 Claims, 6 Drawing Sheets

(56) References Cited

U.S. PATENT DOCUMENTS

| | | |
|---|---|---|
| 5,891,392 A | 4/1999 | Monticello et al. |
| 5,914,302 A | 6/1999 | Murch et al. |
| 5,985,929 A | 11/1999 | Kern |
| 6,001,864 A | 12/1999 | Akashi et al. |
| 6,042,818 A | 3/2000 | Bragulla et al. |
| 6,106,774 A | 8/2000 | Monticello et al. |
| 6,123,966 A | 9/2000 | Kross |
| 6,238,682 B1 | 5/2001 | Klofta et al. |
| 6,248,343 B1 | 6/2001 | Jampani et al. |
| 6,325,968 B1 | 12/2001 | Fricker et al. |
| 6,358,906 B1 | 3/2002 | Ochs et al. |
| 6,423,868 B1 | 7/2002 | Carr et al. |
| 6,488,942 B1 | 12/2002 | Ingemann |
| 6,554,620 B1 | 4/2003 | Iwai |
| 6,583,176 B2 | 6/2003 | Arata |
| 6,627,207 B1 | 9/2003 | Petersen |
| 6,627,657 B1 | 9/2003 | Hilgren et al. |
| 6,667,289 B2 | 12/2003 | Harrison et al. |
| 6,803,057 B2 | 10/2004 | Ramirez et al. |
| 6,943,190 B2 | 9/2005 | Fink et al. |
| 6,991,685 B2 | 1/2006 | Kravitz et al. |
| 7,005,451 B1 | 2/2006 | Nevermann et al. |
| 7,041,631 B2 | 5/2006 | Ochs et al. |
| 7,192,601 B2 | 3/2007 | Walker |
| 7,214,651 B2 | 5/2007 | Mohr et al. |
| 7,294,609 B2 | 11/2007 | Saito et al. |
| 7,700,533 B2 | 4/2010 | Egbe et al. |
| 7,745,384 B2 | 6/2010 | Perry et al. |
| 7,824,665 B2 | 11/2010 | Miyamoto et al. |
| 7,985,773 B2 | 7/2011 | Greten et al. |
| 8,034,844 B2 | 10/2011 | Fox et al. |
| 8,388,991 B2 | 3/2013 | Sondgeroth |
| 8,426,634 B2 | 4/2013 | Neas et al. |
| 8,445,717 B2 | 5/2013 | Neas et al. |
| 8,481,480 B1 | 7/2013 | Lam et al. |
| 9,012,681 B2 | 4/2015 | Neas et al. |
| 2001/0009891 A1 | 7/2001 | Murch et al. |
| 2001/0014652 A1 | 8/2001 | Murch et al. |
| 2001/0016604 A1 | 8/2001 | Yu |
| 2001/0036963 A1 | 11/2001 | Behrends et al. |
| 2002/0045666 A1 | 4/2002 | Russo et al. |
| 2002/0090343 A1 | 7/2002 | Moore et al. |
| 2002/0103098 A1 | 8/2002 | Harrison et al. |
| 2002/0119574 A1 | 8/2002 | Berg |
| 2002/0123523 A1 | 9/2002 | Arata |
| 2002/0142051 A1 | 10/2002 | Rochon |
| 2002/0192297 A1 | 12/2002 | Ramirez et al. |
| 2003/0099717 A1 | 5/2003 | Cabrera |
| 2003/0180377 A1 | 9/2003 | Ramirez et al. |
| 2003/0198689 A1 | 10/2003 | Arata |
| 2004/0023822 A1 | 2/2004 | Ochs et al. |
| 2004/0043912 A1 | 3/2004 | Murch et al. |
| 2004/0058878 A1 | 3/2004 | Walker |
| 2004/0171687 A1 | 9/2004 | Kemp et al. |
| 2004/0176267 A1 | 9/2004 | Hobson |
| 2004/0182425 A1 | 9/2004 | Kravitz et al. |
| 2004/0242443 A1 | 12/2004 | Murch et al. |
| 2005/0003994 A1 | 1/2005 | Ochs et al. |
| 2005/0058719 A1 | 3/2005 | Ramirez et al. |
| 2005/0197397 A1 | 9/2005 | Martin |
| 2005/0236017 A1 | 10/2005 | Kravitz et al. |
| 2005/0238728 A1 | 10/2005 | Evans |
| 2005/0274624 A1 | 12/2005 | Arata |
| 2006/0019855 A1 | 1/2006 | Saito |
| 2006/0094838 A1 | 5/2006 | Mohr et al. |
| 2006/0178281 A1 | 8/2006 | Alasri |
| 2006/0193745 A1 | 8/2006 | Arndt et al. |
| 2006/0285995 A1 | 12/2006 | Hobbs et al. |
| 2006/0292196 A1 | 12/2006 | Padiurashvili et al. |
| 2007/0020364 A1 | 1/2007 | Burnett et al. |
| 2007/0027119 A1 | 2/2007 | Ahmed et al. |
| 2007/0042094 A1 | 2/2007 | Warf, Jr. et al. |
| 2007/0048345 A1 | 3/2007 | Huang |
| 2007/0053942 A1 | 3/2007 | Nishibayashi et al. |
| 2007/0056904 A1 | 3/2007 | Hogt |
| 2007/0059380 A1 | 3/2007 | Ramirez et al. |
| 2007/0082832 A1 | 4/2007 | Dicosimo |
| 2007/0148214 A1 | 6/2007 | Cullen |
| 2007/0184016 A1 | 8/2007 | Macinga et al. |
| 2007/0202069 A1 | 8/2007 | Tamareselvy |
| 2007/0238652 A1 | 10/2007 | Kokai-Kun et al. |
| 2007/0258915 A1 | 11/2007 | Kielbania |
| 2007/0269530 A1 | 11/2007 | Arata et al. |
| 2007/0274926 A1 | 11/2007 | Fuls et al. |
| 2007/0275929 A1 | 11/2007 | Fuls et al. |
| 2007/0280901 A1 | 12/2007 | Fuls et al. |
| 2007/0281999 A1 | 12/2007 | Fox et al. |
| 2007/0286878 A1 | 12/2007 | Harruna |
| 2008/0045491 A1 | 2/2008 | Fitchmun |
| 2008/0138438 A1 | 6/2008 | Taylor et al. |
| 2008/0139656 A1 | 6/2008 | Taylor et al. |
| 2008/0199535 A1 | 8/2008 | Taylor et al. |
| 2008/0233069 A1 | 9/2008 | Tamareselvy |
| 2008/0249187 A1 | 10/2008 | Ali et al. |
| 2008/0286223 A1 | 11/2008 | Fuls et al. |
| 2008/0305182 A1 | 12/2008 | Ramirez et al. |
| 2008/0317799 A1 | 12/2008 | Baker et al. |
| 2009/0012174 A1 | 1/2009 | Seitz, Jr. et al. |
| 2009/0061017 A1 | 3/2009 | Pedersen et al. |
| 2009/0145859 A1 | 6/2009 | Man et al. |
| 2009/0176887 A1 | 7/2009 | Vlasaty et al. |
| 2009/0197786 A1 | 8/2009 | Perry et al. |
| 2009/0252775 A1 | 10/2009 | Arndt et al. |
| 2009/0291944 A1 | 11/2009 | Ash et al. |
| 2010/0003343 A1 | 1/2010 | Ramirez et al. |
| 2010/0040608 A1 | 2/2010 | Wahren-Herlenius |
| 2010/0108942 A1 | 5/2010 | Man et al. |
| 2010/0125104 A1 | 5/2010 | Neas et al. |
| 2010/0143496 A1 | 6/2010 | Larson et al. |
| 2010/0151046 A1 | 6/2010 | Okamoto et al. |
| 2010/0159028 A1 | 6/2010 | Shultz |
| 2010/0204323 A1 | 8/2010 | Theiler et al. |
| 2010/0240600 A1 | 9/2010 | Shimamoto et al. |
| 2010/0240752 A1 | 9/2010 | Drellinger et al. |
| 2010/0261792 A1 | 10/2010 | Neas et al. |
| 2010/0286009 A1 | 11/2010 | Vierbaum et al. |
| 2010/0297316 A1 | 11/2010 | Gutzmann et al. |
| 2010/0323895 A1 | 12/2010 | Gamer |
| 2010/0324135 A1 | 12/2010 | Arata |
| 2010/0330196 A1 | 12/2010 | Ramirez et al. |
| 2011/0009484 A1 | 1/2011 | Arata et al. |
| 2011/0027399 A1 | 2/2011 | Shimamoto et al. |
| 2011/0081300 A1 | 4/2011 | Awad |
| 2011/0117178 A1 | 5/2011 | Junginger |
| 2011/0135702 A1 | 6/2011 | Hoffman et al. |
| 2011/0165261 A1 | 7/2011 | Derby et al. |
| 2011/0182958 A1 | 7/2011 | Omidbakhsh |
| 2011/0245219 A1 | 10/2011 | Ionidis |
| 2011/0301070 A1 | 12/2011 | Ochomogo |
| 2011/0305872 A1 | 12/2011 | Li |
| 2012/0018445 A1 | 1/2012 | Mendoza et al. |
| 2012/0021486 A1 | 1/2012 | Dinu |
| 2012/0125377 A1 | 5/2012 | Perlman et al. |
| 2012/0128719 A1 | 5/2012 | Baker, Jr. et al. |
| 2012/0141600 A1 | 6/2012 | Taylor et al. |
| 2012/0213835 A1 | 8/2012 | Neas et al. |
| 2012/0230869 A1 | 9/2012 | Ramirez et al. |
| 2012/0276219 A1 | 11/2012 | Taylor et al. |
| 2012/0301556 A1 | 11/2012 | Norton |
| 2013/0018097 A1 | 1/2013 | Bolduc et al. |
| 2013/0023582 A1 | 1/2013 | Shimamoto et al. |
| 2013/0037048 A1 | 2/2013 | Edgington et al. |
| 2013/0089533 A1 | 4/2013 | Zhu et al. |
| 2013/0095184 A1 | 4/2013 | Lyczak et al. |
| 2013/0142856 A1 | 6/2013 | Worthington et al. |
| 2013/0150313 A1 | 6/2013 | Flury et al. |
| 2013/0184267 A1 | 7/2013 | Ash et al. |
| 2013/0210767 A1 | 8/2013 | Gamer |
| 2013/0224307 A1 | 8/2013 | Neas et al. |
| 2013/0251820 A1 | 9/2013 | Neas et al. |
| 2013/0330397 A1 | 12/2013 | Neas et al. |
| 2014/0011766 A1 | 1/2014 | Krafft |

(56) References Cited

U.S. PATENT DOCUMENTS

2014/0024688 A1   1/2014   Callahan et al.
2014/0134224 A1   5/2014   Mallet et al.
2015/0196526 A1   7/2015   Neas et al.

FOREIGN PATENT DOCUMENTS

| WO | 2011036628  | 3/2011  |
| WO | 2011129829  | 10/2011 |
| WO | 2012112951  | 8/2012  |
| WO | 20150120216 | 8/2015  |

OTHER PUBLICATIONS

Elder, David P. et al. "Antimicrobial Preservatives Part Two: Choosing a Perservative", American Pharmaceutical Review, Jan. 1, 2012.

COMPOSITIONS AND METHODS HAVING IMPROVED EFFICACY AGAINST SPORES AND OTHER ORGANISMS

CROSS-REFERENCE TO RELATED APPLICATIONS

This application is a continuation of U.S. patent application Ser. No. 15/411,286, filed on Jan. 20, 2017, which is a continuation of U.S. patent application Ser. No. 14/615,691, filed on Feb. 6, 2015, which claims the benefit of U.S. Provisional Patent Application Ser. No. 61/937,060, entitled "Compositions And Methods Having Improved Efficacy Against Spores And Other Organisms," filed Feb. 7, 2014, the entire disclosures of which are incorporated herein by reference.

TECHNICAL FIELD

Embodiments of the present invention provide compositions and methods having surprising efficacy against bacterial and fungal spores, including *Clostridium difficile* spores. Embodiments are also useful against conformationally altered prions, bacteria, fungi, and viruses. Embodiments of the present invention provide acidified alcoholic compositions containing one or more peracids.

BACKGROUND OF THE INVENTION

Different types of organisms vary in their response to antiseptics and disinfectants. The microbial susceptibility to antiseptics and disinfectants of various organisms has been summarized as shown in the following schematic. McDonnell, Gerald et al., "Antiseptics and Disinfectants: Activity, Action, and Resistance," Clinical Microbiology Reviews, Vol. 12, pp. 147-179 (January 1999). Organisms are listed in descending order of resistance.

Prions (CJD, BSE)
↓
Coccidia (*Cryptosporidium*)
↓
Spores (*Bacillus, C. difficile*)
↓
Mycobacteria (*M. tuberculosis, M. avium*)
↓
Cysts (*Giardia*)
↓
Small non-enveloped viruses (Polio virus)
↓
Trophozoites (*Acanthamoeba*)
↓
Gram-negative bacteria (non-sporulating) (*Pseudomonas, Providencia*)
↓
Fungi (*Candida, Aspergillus*)
↓
Large non-enveloped viruses (Enteroviruses, Adenovirus)
↓
Gram-positive bacteria (*S. aureus, Enterococcus*)
↓
Lipid enveloped viruses (HIV, HBV)

Bacterial spores of the genera *Bacillus* and *Clostridium* have been widely studied and are considered to be the most resistant of all types of bacteria to antiseptics and disinfectants.

*Clostridium* species are significant pathogens. Infections among patients in healthcare facilities caused by the bacteria *Clostridium difficile* (*C. difficile*), are at historically high levels. *C. difficile* is a spore-forming, Gram-positive anaerobic *bacillus* of the human intestine and is thought to be present in 2-5% of the adult population. Pathogenic *C. difficile* strains produce multiple toxins, the most well-characterized of which are enterotoxin (*Clostridium difficile* toxin A) and cytotoxin (*C. difficile* toxin B), both of which can produce diarrhea and inflammation in infected patients. The emergence of a new, highly toxic strain of *C. difficile*, resistant to flouroquinolone antibiotics, such as ciprofloxacin and levofloxacin have also been reported. *C. difficile* infection causes diarrhea and other intestinal problems and is linked to 14,000 deaths in the United States each year.

Control of *C. difficile* outbreaks present significant challenges to health care facilities. *C. difficile* spores survive routine environmental cleaning with detergents and hand hygiene with alcohol-based gels. The spores can survive on surfaces for long periods of time. As a result, the bacteria can be cultured from almost any surface. Once spores are ingested, their acid-resistance allows them to pass through the stomach unscathed. They germinate and multiply into vegetative cells in the colon upon exposure to bile acids.

A variety of strategies have been proposed to kill *C. difficile* spores on various surfaces, with limited success. Bleach-based compositions have been employed for hard surfaces, and have been shown to reduce the environmental burden of *C. difficile* but can be corrosive. Hydrogen peroxide-based compositions have also been proposed, including combinations of hydrogen peroxide and peracetic acid, a combination of hydrogen peroxide and silver cation dry-mist system, and the so-called Accelerated Hydrogen Peroxide (AHP). Peracids generally have poor stability, odor and corrosive properties. Hydrogen peroxide is also prone to decomposition, and concentrated solutions can be highly corrosive. Alcohol-based sanitizers have not generally been effective. In fact, ethanol is sometimes used to store *C. difficile* spores.

A need remains for more stable, less corrosive compositions having good efficiency against *C. difficile* spores, as well as against other pathogenic infectious agents such as bacteria, fungi, viruses, fungal and bacterial spores, and conformationally altered prions, some of which can be particularly resistant to current sanitizers and cleansers.

Somewhat relatedly, there is growing concern about the use of biological toxins and infectious agents such as conformationally altered prions, bacteria, viruses, and fungal and bacterial spores, as biological and chemical warfare agents. Chemical and biological warfare agents can be fast-acting and pervasive. There is a continuing need for effective, easy to use products that will be safe for humans and the environment, that can be used to decontaminate skin, and particularly wounds, following chemical and/or biological warfare agent exposure. Furthermore, there is a need for effective products that can be used to decontaminate homes, building materials, and furniture that can decontaminate surfaces to eliminate these infectious agents, and that can reduce the transmission of the infectious pathogens.

DETAILED DESCRIPTION OF ILLUSTRATIVE EMBODIMENTS

In one or more embodiments, the present invention provides a disinfectant composition. The physical form of the disinfectant composition is not particularly limited, and in one or more embodiments, the composition may be presented as a liquid that is poured, pumped, sprayed, or otherwise dispensed, a gel, an aerosol, or a foam, including both aerosol and non-aerosol foams. The disinfectant composition of the present invention may be employed on a wide variety of surfaces or substrates, including hard surfaces, soft surfaces, non-living surfaces, living tissue, skin, soil, porous, and non-porous surfaces. The compositions of the invention may be employed to disinfect or otherwise sanitize inanimate objects such as instruments, medical and military equipment, furniture, handrails, textiles, etc. In one or more embodiments, the disinfectant composition may be presented as a wipe, i.e. a tissue or cloth that is wiped over a surface.

The disinfectant composition comprises at least one alcohol. In one or more embodiments, the alcohol is a $C_{1-6}$ alcohol, i.e. an alcohol containing 1 to 6 carbon atoms. Such alcohols may be referred to as lower alkanols. Typically, these alcohols have antimicrobial properties. Examples of lower alkanols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the disinfectant compositions comprise a mixture of alcohols. In one or more embodiments, the disinfectant compositions comprise a mixture of ethanol and isopropanol. In one or more embodiments, the disinfectant compositions comprise a mixture of isopropanol and n-propanol.

Generally, the disinfectant composition comprises at least about 10 percent by weight (wt. %) alcohol, based upon the total weight of the disinfectant composition. In one embodiment, the disinfectant composition comprises at least about 15 weight percent alcohol, in another embodiment, the disinfectant composition comprises at least about 20 weight percent alcohol, in another embodiment, the disinfectant composition comprises at least about 25 weight percent alcohol, in yet another embodiment, the disinfectant composition comprises at least about 30 weight percent alcohol, and in still yet another embodiment, the disinfectant composition comprises at least about 40 weight percent alcohol, based upon the total weight of disinfectant composition. In one embodiment, the disinfectant composition comprises at least about 50 weight percent alcohol, in another embodiment, the disinfectant composition comprises at least about 60 weight percent alcohol, in another embodiment, the disinfectant composition comprises at least about 65 weight percent alcohol, in yet another embodiment, the disinfectant composition comprises at least about 70 weight percent alcohol, and in still yet another embodiment, the disinfectant composition comprises at least about 78 weight percent alcohol, based upon the total weight of disinfectant composition. More or less alcohol may be required in certain instances, depending particularly on other ingredients and/or the amounts thereof employed in the composition. In certain embodiments, the disinfectant composition comprises from about 10 weight percent to about 98 weight percent alcohol, in other embodiments, the disinfectant composition comprises from about 15 weight percent to about 95 weight percent of alcohol, in yet other embodiments, the disinfectant composition comprises from about 20 weight percent to about 90 weight percent of alcohol, and in still other embodiments, the disinfectant composition comprises from about 30 weight percent to about 85 weight percent of alcohol, based upon the total weight of the disinfectant composition. In certain embodiments, the disinfectant composition comprises from about 50 weight percent to about 98 weight percent alcohol, in other embodiments, the disinfectant composition comprises from about 60 weight percent to about 95 weight percent of alcohol, in yet other embodiments, the disinfectant composition comprises from about 65 weight percent to about 90 weight percent of alcohol, and in still other embodiments, the disinfectant composition comprises from about 70 weight percent to about 85 weight percent of alcohol, based upon the total weight of the disinfectant composition.

In any of the above embodiments, the disinfectant composition may further include a peracid. Examples of peracids include $C_1$-$C_{12}$ percarboxylic acids, diperoxyglutaric acid, diperoxyadipic acid, diperoxysuccinic acid, diperoxysuberic acid, diperoxymalonic acid, peroxylactic acid, peroxyglycolic acid, peroxyoxalic acid, peroxypyruvic acid (PPA), and mixtures thereof. Examples of peracids also include peroxyoctanoic acid. In one or more embodiments, the peracid is selected from $C_{3-12}$ peracids. In one or more embodiments, the peracid is selected from $C_{3-10}$ peracids. In one or more embodiments, the disinfecting compositions include a mixture of peracids. In one or more embodiments, the peracid comprises peroxypyruvic acid. In one or more embodiments, the disinfecting compositions include a peracid other than peracetic acid. In other embodiments, the disinfecting compostions include a peracid in addition to peracetic acid. See U.S. Pat. Nos. 4,051,058, 4,051,059, 5,200,189, 5,200,198, 5,489,434, 5,718,910, 5,314,687, 5,437,868, and U.S. Pub. Pat. App. Nos. 2010/0261792 A1 and 2012/0213835 A1 for further discussion on peracids. These patents are incorporated herein by reference in their entirety.

In one embodiment, the peracid is added to the disinfectant composition as a solution or emulsion. In other words, the peracid may be premixed with a carrier, and optionally one or more other ingredients, to form a peracid solution or emulsion, with the proviso that the carrier does not deleteriously affect the sporicidal properties of the composition. More specifically, a carrier deleteriously affects the sporicidal properties of the composition when it decreases the log kill by more than a de minimus amount. By de minimus is meant a decrease of less than about 0.5 log kill.

Examples of carriers include water, alcohol, or blends of water and another carrier such as glycols, ketones, linear and/or cyclic hydrocarbons, triglycerides, carbonates, silicones, alkenes, esters such as acetates, benzoates, fatty esters, glyceryl esters, ethers, amides, polyethylene glycols, PEG/PPG copolymers, inorganic salt solutions such as saline, and mixtures thereof. It will be understood that, when the peracid is premixed to form a peracid solution or emulsion, the amount of solution or emulsion that is added to the disinfectant composition is selected so that the amount of peracid falls within the ranges set forth hereinabove.

Advantageously, a synergistic antimicrobial and/or sporicidal effect is observed when the peracid is combined with alcohol at an acidic pH. In certain embodiments, peracids that exhibit little or no efficacy on their own against *C. difficile* spores or other resistant organisms provide an enhanced efficacy when combined with alcohol according to the present invention, and a further enhanced efficacy when the pH of the disinfectant composition is less than 7. It has surprisingly been found that, while disinfectant compositions show little or no efficacy against some bacterial or fungal spores, the combination of an enhancer and alcohol at a low pH exhibits synergistically enhanced efficacy against the spores, such *C. difficile* spores. Also, it has been unexpectedly found that the methods of the present invention provide good efficacy against *C. difficile* spores at much lower concentrations of peracid than what is generally thought to be required for good efficacy.

In one or more embodiments, the amount of peracid is 2 weight percent (wt. %) or less, in other embodiments, 1.5 wt. % or less, in other embodiments, 1 wt. % or less, in other embodiments, 0.9 wt. % or less, based upon the total weight of the disinfectant composition.

In one or more embodiments, the peracid may be present in an amount of at least about 100 parts per million by weight (ppm), based upon the total weight of the disinfectant composition, in other embodiments, at least about 200 ppm, in other embodiments, at least about 500 ppm, in other embodiments, at least about 1000 ppm, based upon the total weight of the disinfectant composition.

In one or more embodiments, the peracid may be present in an amount of from about 100 ppm to about 2 weight percent (wt. %), based upon the total weight of the disinfectant composition. In other embodiments, the amount of peracid is from about 200 ppm to about 1.5 wt. %, and in yet other embodiments, from about 500 ppm to about 1 wt. %, based upon the total weight of the disinfectant composition. These amounts, which are lower than what is found in previous peracetic acid-based products and other peracid-based products, are safer for use on skin. For example, many previous surface disinfectants that are based upon a combination of peracetic acid and bleach recommend that the user wear gloves while using the product to avoid skin contact.

In one or more of the above embodiments, the pH of the disinfectant composition is less than about 5; in one or more embodiments, the pH of the disinfectant composition is less than about 4.5; in one or more embodiments, the pH of the disinfectant composition is less than about 4; in one or more embodiments, the pH of the disinfectant composition is less than about 3.5; in one or more embodiments, the pH of the disinfectant composition is less than about 3; in one or more embodiments, the pH of the disinfectant composition is less than about 2.5; in one or more embodiments, the pH of the disinfectant composition is less than about 2.

In one or more of the above embodiments, the pH of the disinfectant composition is from about 0 to about 5. In one or more of the above embodiments, the pH of the disinfectant composition from about 0.5 to about 3. In one or more of the above embodiments, the pH of the disinfectant composition from about 1 to about 2. The disinfectant composition may therefore be referred to as acidified, since the disinfectant composition has an acidic pH.

The disinfectant composition may be acidified by the addition of one or more acids. The type of acid is not limited, however, weak acids are not preferred. The acid should have a pKa of 5.4 (the pKa of citric acid) or less.

Examples of useful acids include mineral acids and organic acids. Mineral acids include, without limitation, hydrochloric acid, nitric acid, phosphoric acid, phosphonic acid, boric acid, and sulfuric acid. Organic acids include sulfonic acids, organophosphorus acids, carboxylic acids such as benzoic acids, propionic acids, phthalic acids, butyric acids, acetic acids, amino acids, and other substituted and unsubstituted organic acids.

Examples of organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxoglutaric acid, dl-glyceric acid, and 2,5 furandicarboxylic acid.

It has been found that acidifying the disinfectant composition enhances the efficacy of the alcoholic solutions against one or more microorganisms. In one or more embodiments, acidifying the disinfectant composition enhances the efficacy of the alcoholic solutions against one or more types of bacterial or fungal spores. In one or more embodiments, acidifying the disinfectant composition enhances the efficacy of the alcoholic solutions against C. difficile.

The composition can further comprise a wide range of optional ingredients, with the proviso that they do not deleteriously affect the sanitizing efficacy of the composition. By deleterious is meant that the decrease in the log reduction is not de minimus, or in other words, the log reduction of C. difficile spores does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emollients, emulsifiers, external analgesics, film formers, foam surfactants, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

It has been discovered that the combination of alcohol and peracid exhibits enhanced antimicrobial efficacy. Advantageously, auxiliary antimicrobials, some of which can be harsh on skin, are not required. In certain embodiments, the disinfectant composition does not contain any auxiliary antimicrobial ingredients. Any antimicrobial ingredient other than the combination of alcohol, peracid and acid may be referred to as an auxiliary antimicrobial agent. In one embodiment, the amount of auxiliary antimicrobial agent (including preservatives) is less than about 0.1 wt. %, in another embodiment, less than about 0.05 wt. %, based upon the total weight of the disinfectant composition. In another embodiment, the disinfectant composition is devoid of auxiliary antimicrobial agents.

It is envisioned that, in other embodiments, auxiliary antimicrobial agents could be included, with the proviso that the antimicrobial ingredient does not deleteriously affect the sanitizing properties of the composition. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; ADBAC, also known as alkyldiethylbenzylammonium chloride, or mixtures of ADBAC with other quat compounds, chlorhexidine salts including chlorhexidine gluconate and the salts of N,N"-Bis(4-chlorophenyl)-3,12-diimino-2,4,11,14-tetraazatetradecanediimidi amide; dodecyl dimethyl ammonium chloride (DDAC); 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, $C_{6-20}$ diols, including $C_{6-12}$-alkane diols such as hexanediol, octanediol, and decanediol, glyceryl caprylate/caprate (GCC), and mixtures thereof. In one or more embodiments, the auxiliary antimicrobial agent(s) are present in an amount of from about 0 to about 2 wt. %, in other embodiments, from about 0.005 to about 1.5 wt. %, in other embodiments, from about 0.1 to about 1 wt. %, based upon the total weight of the disinfectant composition.

Advantageously, certain ingredients that have been designated as critical to current sporicidal compositions can be limited in the disinfectant composition of the present invention. For example, hypochlorous acid and precursors thereof are not necessary, and can be limited, if desired, to less than about 0.5 wt. %, or in another embodiment to less than about 0.1 wt. %, based upon the total weight of the disinfectant composition. In another embodiment, the disinfectant composition is devoid of hypochlorous acid.

In one or more embodiments, the compositions of the present invention may further include peracetic acid. However, in one or more embodiments, the peracid described hereinabove is not peracetic acid. In fact, the disinfectant composition may be devoid of peracetic acid or the amount of peracetic acid may be limited to less than about 0.5 wt. %, in other embodiments, to less than about 0.1 wt. %, based upon the total weight of the disinfectant composition.

Indeed, any component other than the alcohol and peracid is not necessary to achieve antimicrobial efficacy and can optionally be limited to less than about 0.5 wt. %, if desired to less than about 0.1 wt. %, if desired to less than about 0.01 wt. %, or if desired to less than about 0.001 wt. %. It will be understood that the balance of the disinfectant composition may, in certain embodiments, include water or other suitable solvent. In one embodiment, the disinfectant composition is devoid of any component other than alcohol, peracid, acidifier, and optionally water or other suitable solvent.

The disinfectant composition may be prepared by simply mixing the components together. In one embodiment, where one or more components is obtained as a solid powder, the disinfectant composition is prepared by a method comprising dispersing the solid powder in water or alcohol with slow to moderate agitation, and then adding other ingredients as desired, and mixing until the mixture is homogeneous.

Advantageously, it has been found that compositions according to the present invention have efficacy against a broad spectrum of gram positive and gram negative bacteria, fungi, parasites, fungal and bacterial spores, enveloped and non-enveloped viruses, and prions (CJD, CWD, BSE, Scrapie). One or more embodiments of the present invention exhibit efficacy against one or more of spores of *Bacillus anthracis, Bacillus cereus, Clostridium difficile, Clostridium botulinum*, and *Clostridium tetani*.

Unexpectedly, when a peracid is combined with alcohol at a low pH, according to the present invention, sporicidal activity is enhanced, i.e. potentiated. In one or more embodiments, the disinfectant composition is effective at killing *C. difficile* spores. In one or more embodiments, the disinfectant composition is also effective in killing gram negative and gram positive bacteria, fungi, parasites, non-enveloped and enveloped viruses. In one or more embodiments, the disinfectant composition has rapid antimicrobial efficacy against bacteria such as *Staphylococcus aureus*, methicillin-resistant *S. aureus, Escherichia coli, Pseudomonas aeruginosa, Serratia marcescens*, and fungi such as *Candida albicans* and *Aspergillus niger*, and black mold spores *Stachybotrys chartanim*. In one or more embodiments, the disinfectant composition has rapid efficacy against skin microflora, including resident and transient skin microflora.

Thus, the present invention further provides a method for killing or inactivating microbes on a surface comprising applying, to the surface, an effective amount of a disinfectant composition as described herein. Advantageously, the disinfectant composition of the present invention may be used as a healthcare personnel hand wash. In one or more embodiments, the present invention provides an disinfectant composition that meets the standards of the FDA Tentative Final Monograph for Healthcare Antiseptic Drug Products (TFM) (Federal Register 59 [116], Jun. 17, 1994: pp. 31402-31452) for healthcare personnel hand wash, which is incorporated by reference herein.

The disinfectant composition and method of the present invention provides rapid antimicrobial efficacy upon a single use, without requiring auxiliary antimicrobial agents. The rapid, broad-spectrum efficacy makes the compositions useful as skin preparations as described and tested in ASTM E 1173-01 provides "Standard Test Method for Evaluation of Preoperative, Precatheterization, or Preinjection Skin Preparations" and FDA Tentative Final Monograph for Healthcare Antiseptic Drug Products (TFM) (Federal Register 59 [116], Jun. 17, 1994: pp. 31402-31452), which is incorporated by reference herein.

In one or more embodiments, the present invention provides a disinfectant composition that meets the standards of one or more of EN1040 for basic bactericidal activity, EN1275 for basic fungicidal activity, EN1500 for activity of products for use as a hygienic hand rub, EN 14348 for tuberculoidal activity, EN 14476 for virucidal activity, and EN12791 for surgical hand disinfection.

Thus, the present invention further provides a method for killing or inactivating organisms on a surface comprising applying, to the surface, an effective amount of a disinfectant composition as described herein. The disinfectant composition may be employed on a wide variety of surfaces or substrates, including hard surfaces, soft surfaces, skin, porous, and non-porous surfaces.

In one or more embodiments, the method provides a log reduction against spores of at least about 1 in less than about 1 minute. In other embodiments, the method provides a log reduction against spores of at least about 1.5 in less than about 1 minute. In yet other embodiments, the method provides a log reduction against spores of at least about 2 in less than about 1 minute. In other embodiments, the method provides a log reduction against spores of at least about 2.5 in less than about 1 minute. In yet other embodiments, the method provides a log reduction against spores of at least about 3 in less than about 1 minute.

In one or more embodiments, the method provides a log reduction against spores of at least about 1 in less than about 30 seconds. In other embodiments, the method provides a log reduction against spores of at least about 1.5 in less than about 30 seconds. In yet other embodiments, the method provides a log reduction against spores of at least about 2 in less than about 30 seconds. In other embodiments, the method provides a log reduction against spores of at least about 2.5 in less than about 30 seconds. In yet other embodiments, the method provides a log reduction against spores of at least about 3 in less than about 30 seconds.

In one or more embodiments, the method provides a log reduction against spores on inanimate, hard, non-porous surfaces of at least about 6 in 10 minutes or less. In other embodiments, the method provides a log reduction against spores of at least about 6 in about 7 minutes or less. In yet other embodiments, the method provides a log reduction against spores of at least about 6 in about 6 minutes or less. In other embodiments, the method provides a log reduction against *C. difficile* spores on inanimate, hard, non-porous surfaces of at least about 6 in about 10 minutes or less. In yet other embodiments, the method provides a log reduction against *C. difficile* spores on inanimate, hard, non-porous surfaces of at least about 6 in about 7 minutes or less. In yet other embodiments, the method provides a log reduction against *C. difficile* spores on inanimate, hard, non-porous surfaces of at least about 6 in about 6 minutes or less.

In one or more embodiments, the method provides a log reduction against *C. difficile* spores of at least about 1 in less than about 1 minute. In other embodiments, the method provides a log reduction against *C. difficile* spores of at least about 1.5 in less than about 1 minute. In yet other embodiments, the method provides a log reduction against *C. difficile* spores of at least about 2 in less than about 1 minute. In other embodiments, the method provides a log reduction against *C. difficile* spores of at least about 2.5 in less than about 1 minute. In yet other embodiments, the method provides a log reduction against *C. difficile* spores of at least about 3 in less than about 1 minute.

In one or more embodiments, the method provides a log reduction against *C. difficile* spores of at least about 1 in less than about 30 seconds. In other embodiments, the method provides a log reduction against *C. difficile* spores of at least about 1.5 in less than about 30 seconds. In yet other embodiments, the method provides a log reduction against *C. difficile* spores of at least about 2 in less than about 30 seconds. In other embodiments, the method provides a log reduction against *C. difficile* spores of at least about 2.5 in less than about 30 seconds. In yet other embodiments, the method provides a log reduction against *C. difficile* spores of at least about 3 in less than about 30 seconds.

Advantageously, the rapid efficacy of the methods and compositions of the present invention make it feasible to utilize them for skin/hand disinfection.

In one or more embodiments, the method provides a log reduction against *C. difficile* spores on skin of at least about 1 in less than about 1 minute. In other embodiments, the method provides a log reduction against *C. difficile* spores on skin of at least about 1.5 in less than about 1 minute. In yet other embodiments, the method provides a log reduction of *C. difficile* spores on skin of at least about 2 in less than about 1 minute. In other embodiments, the method provides a log reduction against *C. difficile* spores on skin of at least about 2.5 in less than about 1 minute. In yet other embodiments, the method provides a log reduction against *C. difficile* spores on skin of at least about 3 in less than about 1 minute.

In one or more embodiments, the method provides a log reduction against *C. difficile* spores on skin of at least about 1 in less than about 30 seconds. In other embodiments, the method provides a log reduction against *C. difficile* spores on skin of at least about 1.5 in less than about 30 seconds. In yet other embodiments, the method provides a log reduction against *C. difficile* spores on skin of at least about 2 in less than about 30 seconds. In other embodiments, the method provides a log reduction against *C. difficile* spores on skin of at least about 2.5 in less than about 30 seconds. In yet other embodiments, the method provides a log reduction against *C. difficile* spores on skin of at least about 3 in less than about 30 seconds.

The methods of the present invention include the step of applying a disinfectant composition to a surface.

Advantageously, good efficacy is achieved by the methods of the present invention when the disinfectant composition is applied to the surface at standard temperature and at close to standard pressure. In one or more embodiments, the temperature of the disinfectant composition when applied to the surface may be less than about 150° F., in other embodiments, less than about 120° F., and in other embodiments, less than about 105° F. In one or more embodiments, the temperature of the disinfectant composition may be in the range of from about 40° F. to about 150° F., in other embodiments in the range of from about 40° F. to about 105° F., and in other embodiments, in the range of about 70° F. to 105° F.

Although the liquid disinfectant compositions of the present invention may be applied to the surface to be cleaned by spraying, no high pressure application is required. During this step, the disinfectant composition may be brought into contact with the target surface in bursts or in a continuous manner by circulating, flooding, spraying, foaming or fogging. The step may also be carried out by forming a two phase annular mist of antimicrobial treatment solution and air.

Advantageously, the methods of the present invention provide good efficacy against spores within 10 minutes or less. Embodiments of the invention provide good efficacy against spores within 7 minutes or less. Embodiments of the invention provide good efficacy against spores within 6 minutes or less. Embodiments of the invention provide good efficacy against spores within 5 minutes or less. Embodiments of the invention provide good efficacy against spores within 2 minutes or less. Embodiments of the invention provide good efficacy against spores within 1 minute or less. Embodiments of the invention provide good efficacy against spores within 30 seconds or less. Advantageously, the methods of the present invention provide good efficacy against *C. difficile* spores within 5 minutes or less. Embodiments of the invention provide good efficacy against *C. difficile* spores within 2 minutes or less.

In one or more embodiments, the method provides a log reduction against spores, such as *C. difficile*, of at least about 1 in less than about 1 minute. In other embodiments, the method provides a log reduction against spores of at least about 1.5 in less than about 1 minute. In yet other embodiments, the method provides a log reduction against spores of at least about 2 in less than about 1 minute. In other embodiments, the method provides a log reduction against spores of at least about 2.5 in less than about 1 minute. In yet other embodiments, the method provides a log reduction against spores of at least about 3 in less than about 1 minute.

In one or more embodiments, the method provides a log reduction against spores of at least about 1 in less than about 30 seconds. In other embodiments, the method provides a log reduction against spores of at least about 1.5 in less than about 30 seconds. In yet other embodiments, the method provides a log reduction against spores of at least about 2 in less than about 30 seconds. In other embodiments, the method provides a log reduction against spores of at least about 2.5 in less than about 30 seconds. In yet other embodiments, the method provides a log reduction against spores of at least about 3 in less than about 30 seconds.

Advantageously, the methods of the present invention provide good efficacy against *C. difficile* spores within 5 minutes or less. Embodiments of the invention provide good efficacy against *C. difficile* spores within 2 minutes or less. Embodiments of the invention provide good efficacy against *C. difficile* spores within 1 minute or less. Embodiments of the invention provide good efficacy against *C. difficile* spores within 30 seconds or less. Thus, in one or more embodiments, the duration of contact of the disinfectant composition with the target surface is from about 20 seconds to 5 minutes, in other embodiments, from about 25 seconds to about 2 minutes, and in other embodiments, from about 30 seconds to about 1 minute. It will be understood that, in some embodiments, a longer contact time is advantageous, and in one or more embodiments, the contact time may be up to 30 minutes, and in other embodiments, up to about 60 minutes.

The amount of disinfectant composition to be applied to the target surface is not particularly limited. At a minimum, a sufficient amount of disinfectant composition should be applied to substantially wet the surface such that the surface will remain wet for the desired contact time, noting that there will be some evaporation of the disinfectant composition.

Any amount of the disinfectant composition may be used for each application, so long as it is at least an effective amount to contact substantially the entire target surface and keep it wet for at least 30 to 60 seconds. In one or more embodiments, the amount of the disinfectant composition is sufficient to contact substantially the entire target surface and keep it wet for a contact time of at least 5 minutes. In one or more embodiments, the amount of the disinfectant composition is sufficient to contact substantially the entire target surface and keep it wet for a contact time of at least 6 minutes. In one or more embodiments, the amount of the disinfectant composition is sufficient to contact substantially the entire target surface and keep it wet for a contact time of at least 7 minutes. In one or more embodiments, the amount of the disinfectant composition is sufficient to contact substantially the entire target surface and keep it wet for a contact time of at least 10 minutes. In one or more embodiments, the amount of the disinfectant composition is sufficient to contact substantially the entire target surface and keep it wet for a contact time of at least 30 minutes. In one or more embodiments, the amount of the disinfectant composition is sufficient to contact substantially the entire target surface and keep it wet for at least 60 minutes.

Advantageously, to minimize any possible instability or degradation of the active components of the compositions of the present invention, the compositions of the present invention may be generated at the time of use.

In one or more embodiments, the sporicidal disinfectant composition may be prepared by combining two or more liquid pre-mix compositions. A first pre-mix composition may comprise a concentrate of the peracid, a second pre-mix composition may comprise a concentrate of the alcohol, and the acidifying agent may be present in either or both pre-mixes, such that combination of the pre-mix compositions results in a disinfectant composition comprising alcohol and a peracid at low pH as described hereinabove.

In other embodiments, a first pre-mix composition may comprise a concentrate of the alcohol and peracid, the second pre-mix composition may comprise a diluent, and the acidifying agent may be present in either or both pre-mixes, such that combination of the pre-mix compositions results in a disinfectant composition comprising alcohol and a peracid at the concentrations and pH as described hereinabove.

In one or more embodiments, the pre-mix compositions may be stored in a dual dispenser and mixed only when the dispenser is actuated. The pre-mix components may be dispensed from physically separate packages or from a unitary package having non-communicating chambers. For purposes of this specification, the term dual dispenser apparatus refers to a configuration where multiple liquid pre-mix components are dispensed from a plurality of physically separate packages, and also refers to a configuration where multiple liquid pre-mix components are dispensed from a unitary package having a plurality of non-communicating chambers, each chamber having an orifice through which an aliquot of a component is dispensed.

In one or more embodiments, aliquots of the pre-mix components are dispensed substantially simultaneously, such that the liquid aliquots are commingled. In particular embodiments, the aliquots are dispensed through orifices that are configured to enable the commingling of the aliquots. It will be understood that the dispenser may take a variety of forms, and may include a variety of components and configurations in order to cause the desired comingling of aliquots of the pre-mix components and dispensing of a product.

Figure 1:
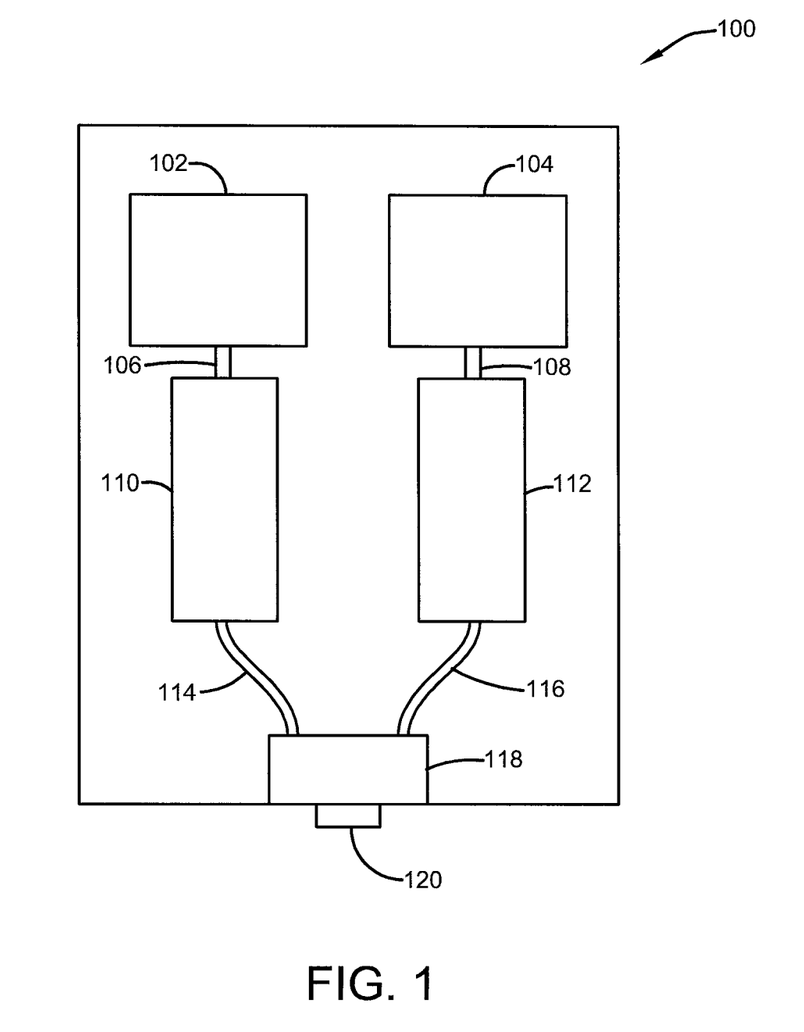
FIG. 1 is a schematic view of a dispenser according to the present invention.

One embodiment of an exemplary dispenser is shown in FIG. 1 and is generally indicated by the numeral 100. Dispenser 100 may include a first reservoir 102 containing a first liquid pre-mix component (e.g. concentrated peracid pre-mix component), and a second reservoir 104 containing a second liquid pre-mix component (e.g. alcoholic diluent pre-mix component). The pH-adjusting agent may be present in either or both of the pre-mix components. As will be apparent to those skilled in the art, and as indicated above, the first and second reservoirs 102 and 104 are not in direct communication with one another, and the first and second pre-mix components are therefore stored separately within the dispenser. Although separate reservoirs are shown in FIG. 1, it is contemplated that the first and second reservoirs 102 and 104 may be provided as physically separate chambers in a single package. Each of the first and second reservoirs 102 and 104 is impervious to fluid transfer therethrough, except through inlet passages 106 and 108, respectively.

Generally, the present invention provides a method of preparing a disinfectant composition, the method comprising the steps of providing a dispenser having a first reservoir containing a first liquid pre-mix that is a concentrated peracid pre-mix, a second reservoir containing a second liquid pre-mix that is an alcoholic pre-mix, wherein the dispenser is adapted to dispense an aliquot of the first pre-mix and an aliquot of the second pre-mix, such that the aliquots commingle. Upon commingling, the aliquots of the first pre-mix and second pre-mix form a disinfectant composition comprising an alcohol and a peracid at a pH of about 5 or less.

In certain embodiments, a first pump 110 may be in fluid communication with the first reservoir 102 through the inlet passage 106, and a second pump 112 may be in fluid communication with the second reservoir 104 through the inlet passage 108. First and second pumps 110 and 112 may be any type of pump known to those skilled in the art and suitable for conveying the first and second liquid pre-mix components from the first and second reservoirs 102 and 104. In one or more embodiments, the pumps 110 and 112 may both be positive displacement pumps. The first and second pumps 110 and 112 discharge the first and second pre-mix components through outlet passages 114 and 116, respectively. In certain embodiments, the output or displacement of the first and second pumps 110 and 112 may be adjustable to vary the rate of fluid flow therethrough. While the exemplary dispenser 100 shown and described includes first and second pumps 110 and 112, it is also contemplated that a single pump may be used, and may be in fluid communication with both the first and second reservoirs 102 and 104.

The outlet passages 114 and 116 may each extend to a mixing nozzle 118 where the first and second pre-mix components are comingled to form a disinfectant composition. The features and dimensions of the mixing nozzle 118 may be adjusted to vary the volume of each pre-mix aliquot, as well as the rate of mixing and comingling of the first and second pre-mix components. The mixing nozzle 118 includes a dispensing passage 120 through which the disinfectant composition is dispensed.

In certain embodiments, the first and second pumps 110 and 112 may be adjusted to produce substantially the same flow rate of the first and second pre-mix components therethrough. In other embodiments, the pumps 110 and 112 may be adjusted to provide different flow rates, and in certain embodiments, the pre-mix components may be dispensed sequentially.

In certain embodiments, the first and second pumps 110 and 112 may be adjusted to select substantially the same aliquot volume for the first and second pre-mix components. In other embodiments, the pumps 110 and 112 may be adjusted to provide different aliquot volumes.

In one or more embodiments, the first and second pumps 110 and 112 may be adapted to dispense a single dose of composition upon actuation. In the same or other embodiments, the first and second pumps 110 and 112 may be adapted to produce a continuous flow of the disinfectant composition upon actuation.

In one or more embodiments, the first pre-mix may include a concentrated form of the compositions of the present invention, and the second pre-mix may include a diluent, such that upon being dispensed, the combination forms a composition that includes the amounts of components taught herein.

Thus, the present invention provides a method of dispensing an efficacious disinfectant composition, including the steps of providing a dual dispenser apparatus, where the dispenser apparatus is configured to dispense multiple liquid pre-mix components from a plurality of physically separate packages, or where the dispenser apparatus is configured to dispense multiple liquid pre-mix components from a unitary package having a plurality of non-communicating chambers, each chamber having an orifice through which an aliquot of a component is dispensed; said dispenser containing a first liquid pre-mix composition that includes a $C_{1-6}$ alcohol and a peracid, said first liquid pre-mix composition having a pH of less than about 5; said dispenser further containing a second liquid pre-mix composition that includes a diluent selected from a $C_{1-6}$ alcohol, water, and mixtures thereof; and actuating said dispenser to commingle an aliquot of said first pre-mix with an aliquot of said second pre-mix and dispense said commingled aliquots.

In one or more embodiments, aliquots of the pre-mix components are dispensed substantially simultaneously, such that the liquid aliquots are commingled.

Advantageously, compositions of the present invention exhibit improved stability under normal conditions of product storage and transport, and therefore exhibit longer shelf life than peroxide-based products and even other peracid-based products that do not contain the synergistic combination of peracid and alcohol at a low pH. Optionally, the compositions of the present invention may be further stabilized by the inclusion of one or more stabilizers. Examples of stabilizers include chelators, inorganic acids and organic acids.

Decomposition of the peracid to peroxide leads to a reduction in efficacy. The peroxide is in turn susceptible to decomposition to water, which leads to a further reduction in efficacy. Reference to stability, within the context of the present invention, means that the peracid does not decompose within the disinfectant composition to peroxide or water during a stated period of time, and when kept within stated conditions of temperature and pressure. Stability can be assessed by direct chemical measurement of the concentration of the peracid, for example by HPLC, and/or can be assessed by measuring the efficacy of the disinfectant composition.

In one or more embodiments, compositions of the present invention are stable, under conditions of standard temperature and pressure for at least 3 days, in other embodiments, for at least 1 week, in other embodiments, for at least 2 weeks, in other embodiments, for at least 1 month, in other embodiments, for at least 2 months, in other embodiments, for at least 6 months, in other embodiments, for at least 1 year. Thus, compositions of the present invention are able to maintain their broad efficacy, including efficacy against viruses, bacterial and fungal spores such as *C. difficile* spores, over longer periods of time, whereas other products would have undergone decomposition and would no longer be as efficacious.

Accordingly, the present invention provides a method of improving the stability of peracid-containing disinfectant compositions, the method including the steps of combining a peracid with a $C_{1-6}$ alcohol, at a pH of less than about 5, to form a stabilized peracid-containing composition, and maintaining the composition in a container or dispenser until ready for use, wherein the stability of the stabilized composition is improved when compared to the stability of the same composition but not containing a $C_{1-6}$ alcohol, and not at a pH of less than about 5.

In order to demonstrate the practice of the present invention, the following examples have been prepared and tested. The examples should not, however, be viewed as limiting the scope of the invention. The claims will serve to define the invention.

EXAMPLES

In the following examples, where peroxypyruvic acid was employed, it was obtained from CHD Bioscience under the tradename VERIOX™. VERIOX™ is a concentrated solution of peroxypyruvic acid in water, and was diluted to achieve the concentrations described below.

Example 1 was a solution of 845 ppm peroxypyruvic acid (PPA) in water, to which 12 N hydrochloric acid had been added to achieve a pH of about 1.5.

Example 2 was a solution of 70 wt. % ethanol and 845 ppm PPA in water, to which 12 N hydrochloric acid had been added to achieve a pH of about 1.5.

Example 3 was a solution of 1690 ppm PPA in water, to which 12 N hydrochloric acid had been added to achieve a pH of about 1.5.

Example 4 was a solution of 70 wt. % ethanol and 1690 ppm PPA in water, to which 12 N hydrochloric acid had been added to achieve a pH of about 1.5.

Example 5 was a solution of 6760 ppm PPA in water, to which 12 N hydrochloric acid had been added to achieve a pH of about 1.5.

Example 6 was a solution of 70 wt. % ethanol and 6760 ppm PPA in water, to which 12 N hydrochloric acid had been added to achieve a pH of about 1.5.

Example 7 was a solution of 845 ppm PPA in water, to which 12 N hydrochloric acid had been added to achieve a pH of about 2.

Example 8 was a solution of 70 wt. % ethanol and 8455 ppm PPA in water, to which 12 N hydrochloric acid had been added to achieve a pH of about 2.

Example 9 was a solution of 1690 ppm PPA in water, to which 12 N hydrochloric acid had been added to achieve a pH of about 2.

Example 10 was a solution of 70 wt. % ethanol and 1690 ppm PPA in water, to which 12 N hydrochloric acid had been added to achieve a pH of about 2.

Example 11 was a solution of 6760 PPA in water, to which 12 N hydrochloric acid had been added to achieve a pH of about 2.

Example 12 was a solution of 70 wt. % ethanol and 6760 ppm PPA in water, to which 12 N hydrochloric acid had been added to achieve a pH of about 2.

Example 13 was a solution of 845 ppm PPA in water, to which 12 N hydrochloric acid had been added to achieve a pH of about 2.5.

Example 14 was a solution of 70 wt. % ethanol and 845 ppm PPA in water, to which 12 N hydrochloric acid had been added to achieve a pH of about 2.5.

Example 15 was a solution of 1690 ppm PPA in water, to which 12 N hydrochloric acid had been added to achieve a pH of about 2.5.

Example 16 was a solution of 70 wt. % ethanol and 1690 ppm PPA in water, to which 12 N hydrochloric acid had been added to achieve a pH of about 2.5.

Example 17 was a solution of 6760 ppm PPA in water, to which 12 N hydrochloric acid had been added to achieve a pH of about 2.5.

Example 18 was a solution of 70 wt. % ethanol and 6790 ppm PPA in water, to which 12 N hydrochloric acid had been added to achieve a pH of about 2.5.

Figure 2:
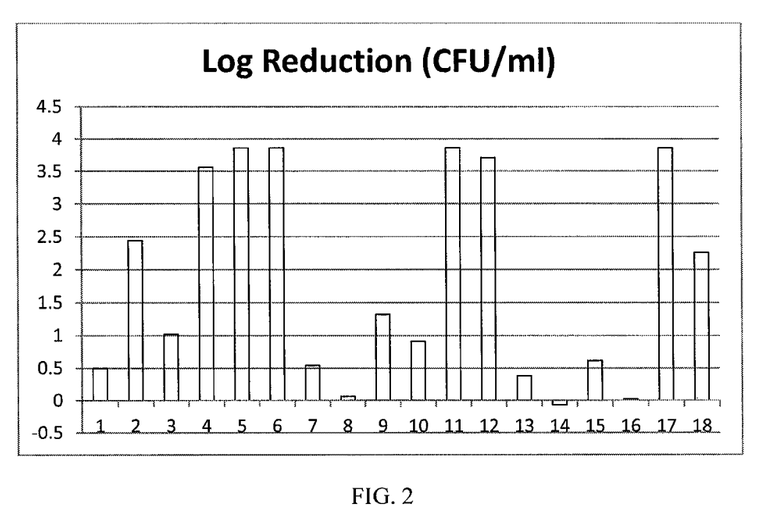
FIG. 2 is a schematic representation of the log reduction (CFU/ml) of *C. difficile* spores for various test compositions, as described herein.

The samples were tested for efficacy against *C. difficile* spores, according to the ASTM E 2315 method, "Standard Guide for Assessment of Antimicrobial Activity Using a Time-Kill Procedure." Contact time was 30 seconds. Results are shown in Table 1 and FIG. 2.

TABLE 1

| Example | Composition | pH | Log Reduction (CFU/ml) |
|---|---|---|---|
| 1 | 845 ppm PPA | 1.5 | 0.5 |
| 2 | 845 ppm PPA + 70% ethanol | 1.5 | 2.44 |
| 3 | 1690 ppm PPA | 1.5 | 1.02 |
| 4 | 1690 ppm PPA + 70% ethanol | 1.5 | 3.56 |
| 5 | 6760 ppm PPA | 1.5 | 3.86 |
| 6 | 6760 ppm PPA + 70% ethanol | 1.5 | 3.86 |
| 7 | 845 ppm PPA | 2 | 0.54 |
| 8 | 845 ppm PPA + 70% ethanol | 2 | 0.06 |
| 9 | 1690 ppm PPA | 2 | 1.32 |
| 10 | 1690 ppm PPA + 70% ethanol | 2 | 0.91 |
| 11 | 6760 ppm PPA | 2 | 3.86 |
| 12 | 6760 ppm PPA + 70% ethanol | 2 | 3.71 |
| 13 | 845 ppm PPA | 2.5 | 0.38 |
| 14 | 845 ppm PPA + 70% ethanol | 2.5 | −0.07 |
| 15 | 1690 ppm PPA | 2.5 | 0.61 |
| 16 | 1690 ppm PPA + 70% ethanol | 2.5 | 0.02 |
| 17 | 6760 ppm PPA | 2.5 | 3.86 |
| 18 | 6760 ppm PPA + 70% ethanol | 2.5 | 2.26 |

Example 19 was a solution of 845 ppm PPA in water, to which 12 N hydrochloric acid had been added to achieve a pH of about 1.5.

Example 20 was a solution of 70 wt. % ethanol in water, to which 12 N hydrochloric acid had been added to achieve a pH of about 1.5.

Example 21 was a solution of 70 wt. % ethanol and 845 ppm PPA in water, to which 12 N hydrochloric acid had been added to achieve a pH of about 1.5.

Example 22 was a solution of 1690 ppm PPA in water, to which 12 N hydrochloric acid had been added to achieve a pH of about 1.5.

Example 23 was a solution of 70 wt. % ethanol in water, to which 12 N hydrochloric acid had been added to achieve a pH of about 1.5.

Example 24 was a solution of 70 wt. % ethanol and 1690 ppm PPA in water, to which 12 N hydrochloric acid had been added to achieve a pH of about 1.5.

Example 25 was a solution of 3380 ppm PPA in water, to which 12 N hydrochloric acid had been added to achieve a pH of about 1.5.

Example 26 was a solution of 70 wt. % ethanol in water, to which 12 N hydrochloric acid had been added to achieve a pH of about 1.5.

Example 27 was a solution of 70 wt. % ethanol and 3380 ppm PPA in water, to which 12 N hydrochloric acid had been added to achieve a pH of about 1.5.

Example 28 was a solution of 845 ppm PPA in water, to which 12 N hydrochloric acid had been added to achieve a pH of about 1.8.

Example 29 was a solution of 70 wt. % ethanol in water, to which 12 N hydrochloric acid had been added to achieve a pH of about 1.8.

Example 30 was a solution of 70 wt. % ethanol and 845 ppm PPA in water, to which 12 N hydrochloric acid had been added to achieve a pH of about 1.8.

Example 31 was a solution of 1690 ppm PPA in water, to which 12 N hydrochloric acid had been added to achieve a pH of about 1.8.

Example 32 was a solution of 70 wt. % ethanol in water, to which 12 N hydrochloric acid had been added to achieve a pH of about 1.8.

Example 33 was a solution of 70 wt. % ethanol and 1690 ppm PPA in water, to which 12 N hydrochloric acid had been added to achieve a pH of about 1.8.

Example 34 was a solution of 3380 ppm PPA in water, to which 12 N hydrochloric acid had been added to achieve a pH of about 1.8.

Example 35 was a solution of 70 wt. % ethanol in water, to which 12 N hydrochloric acid had been added to achieve a pH of about 1.8.

Example 36 was a solution of 70 wt. % ethanol and 3380 ppm PPA in water, to which 12 N hydrochloric acid had been added to achieve a pH of about 1.8.

Figure 3:
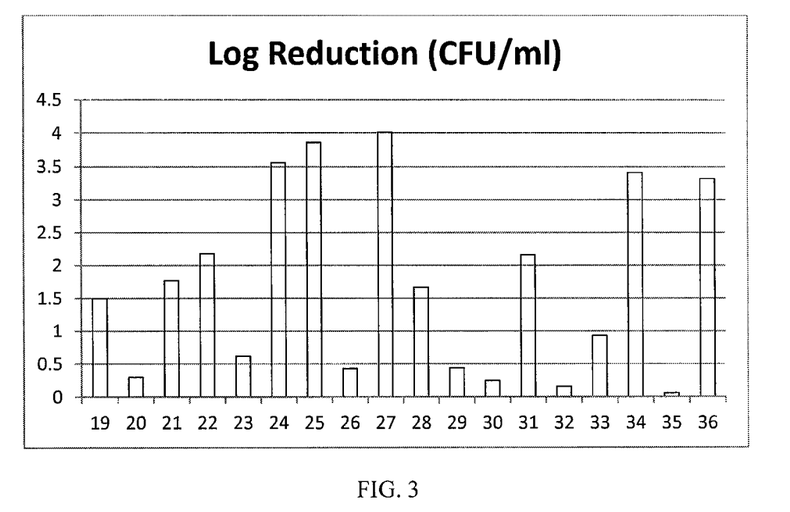
FIG. 3 is a schematic representation of the log reduction (CFU/ml) of *C. difficile* spores for various test compositions, as described herein.

As for Examples 1-18, the samples were tested for efficacy against *C. difficile* spores, according to the ASTM E 2315 method, "Standard Guide for Assessment of Antimicrobial Activity Using a Time-Kill Procedure." Contact time was 30 seconds. Results are shown in Table 2 and FIG. 3.

TABLE 2

| Example | Composition | pH | Log Reduction (CFU/ml) |
|---|---|---|---|
| 19 | 845 ppm PPA | 1.5 | 1.5 |
| 20 | 70% ethanol | 1.5 | 0.3 |
| 21 | 845 ppm PPA + 70% ethanol | 1.5 | 1.77 |
| 22 | 1690 ppm PPA | 1.5 | 2.18 |
| 23 | 70% ethanol | 1.5 | 0.62 |
| 24 | 1690 ppm PPA + 70% ethanol | 1.5 | 3.56 |
| 25 | 3380 ppm PPA | 1.5 | 3.86 |
| 26 | 70% ethanol | 1.5 | 0.43 |
| 27 | 3380 ppm PPA + 70% ethanol | 1.5 | 4.01 |
| 28 | 845 ppm PPA | 1.8 | 1.67 |
| 29 | 70% ethanol | 1.8 | 0.44 |
| 30 | 845 ppm PPA + 70% ethanol | 1.8 | 0.25 |
| 31 | 1690 ppm PPA | 1.8 | 2.16 |
| 32 | 70% ethanol | 1.8 | 0.16 |
| 33 | 1690 ppm PPA + 70% ethanol | 1.8 | 0.93 |
| 34 | 3380 ppm PPA | 1.8 | 3.41 |
| 35 | 70% ethanol | 1.8 | 0.06 |
| 36 | 3380 ppm PPA + 70% ethanol | 1.8 | 3.32 |

Example 37 was a solution of 70 wt. % ethanol in water, to which 12 N hydrochloric acid had been added to achieve a pH of about 1.5.

Example 38 was a solution of 845 ppm PPA in water, to which 12 N hydrochloric acid had been added to achieve a pH of about 1.5.

Example 39 was a solution of 70 wt. % ethanol and 845 ppm PPA in water, to which 12 N hydrochloric acid had been added to achieve a pH of about 1.5.

Example 40 was a solution of 70 wt. % ethanol in water, to which 12 N hydrochloric acid had been added to achieve a pH of about 1.5.

Example 41 was a solution of 845 ppm PPA in water, to which 12 N hydrochloric acid had been added to achieve a pH of about 1.5.

Example 42 was a solution of 70 wt. % ethanol and 845 ppm PPA in water, to which 12 N hydrochloric acid had been added to achieve a pH of about 1.5.

Example 43 was a solution of 70 wt. % ethanol in water, to which 12 N hydrochloric acid had been added to achieve a pH of about 1.5.

Example 44 was a solution of 845 ppm PPA in water, to which 12 N hydrochloric acid had been added to achieve a pH of about 1.5.

Example 45 was a solution of 70 wt. % ethanol and 845 ppm PPA in water, to which 12 N hydrochloric acid had been added to achieve a pH of about 1.5.

Example 46 was a solution of 70 wt. % ethanol in water, to which 12 N hydrochloric acid had been added to achieve a pH of about 1.8.

Example 47 was a solution of 845 ppm PPA in water, to which 12 N hydrochloric acid had been added to achieve a pH of about 1.8.

Example 48 was a solution of 70 wt. % ethanol and 845 ppm PPA in water, to which 12 N hydrochloric acid had been added to achieve a pH of about 1.8.

Example 49 was a solution of 70 wt. % ethanol in water, to which 12 N hydrochloric acid had been added to achieve a pH of about 1.8.

Example 50 was a solution of 845 ppm PPA in water, to which 12 N hydrochloric acid had been added to achieve a pH of about 1.8.

Example 51 was a solution of 70 wt. % ethanol and 845 ppm PPA in water, to which 12 N hydrochloric acid had been added to achieve a pH of about 1.8.

Example 52 was a solution of 70 wt. % ethanol in water, to which 12 N hydrochloric acid had been added to achieve a pH of about 1.8.

Example 53 was a solution of 845 ppm PPA in water, to which 12 N hydrochloric acid had been added to achieve a pH of about 1.8.

Example 54 was a solution of 70 wt. % ethanol and 845 ppm PPA in water, to which 12 N hydrochloric acid had been added to achieve a pH of about 1.8.

Figure 4:
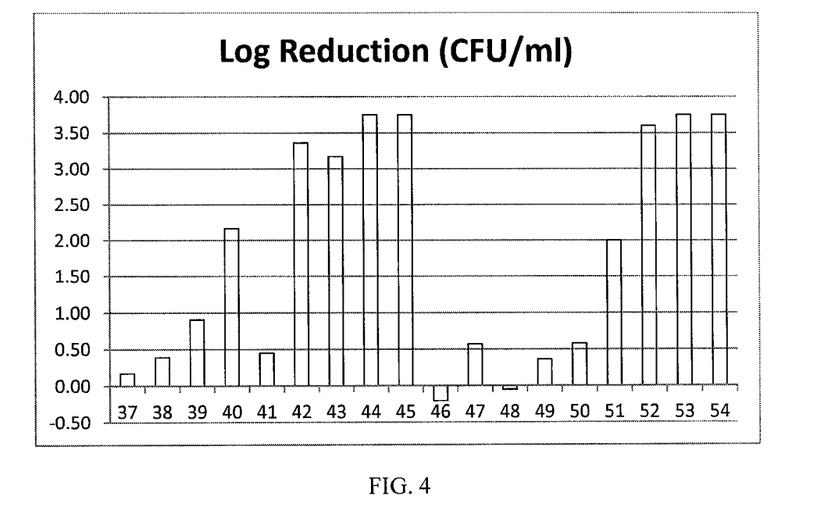
FIG. 4 is a schematic representation of the log reduction (CFU/ml) of *C. difficile* spores for various test compositions, as described herein.

As for Examples 1-18, the samples were tested for efficacy against *C. difficile* spores, according to the ASTM E 2315 method, "Standard Guide for Assessment of Antimicrobial Activity Using a Time-Kill Procedure." Contact time was 30 seconds for examples 37-39 and 46-48, 60 seconds for examples 40-42 and 49-51, and 5 minutes for examples 43-45 and 52-54. Results are shown in Table 3 and FIG. 4.

TABLE 3

| Example | Composition | pH | Exposure Time | Log Reduction (CFU/ml) |
|---|---|---|---|---|
| 37 | 70% ethanol | 1.5 | 30 sec | 0.17 |
| 38 | 845 ppm PPA | 1.5 | 30 sec | 0.39 |
| 39 | 845 ppm PPA + 70% ethanol | 1.5 | 30 sec | 0.91 |
| 40 | 70% ethanol | 1.5 | 60 sec | 2.17 |
| 41 | 845 ppm PPA | 1.5 | 60 sec | 0.45 |
| 42 | 845 ppm PPA + 70% ethanol | 1.5 | 60 sec | 3.36 |
| 43 | 70% ethanol | 1.5 | 5 min | 3.17 |
| 44 | 845 ppm PPA | 1.5 | 5 min | 3.75 |
| 45 | 845 ppm PPA + 70% ethanol | 1.5 | 5 min | 3.75 |
| 46 | 70% ethanol | 1.8 | 30 sec | −0.21 |
| 47 | 845 ppm PPA | 1.8 | 30 sec | 0.57 |
| 48 | 845 ppm PPA + 70% ethanol | 1.8 | 30 sec | −0.05 |
| 49 | 70% ethanol | 1.8 | 60 sec | 0.36 |
| 50 | 845 ppm PPA | 1.8 | 60 sec | 0.58 |
| 51 | 845 ppm PPA + 70% ethanol | 1.8 | 60 sec | 2.00 |
| 52 | 70% ethanol | 1.8 | 5 min | 3.60 |
| 53 | 845 ppm PPA | 1.8 | 5 min | 3.75 |
| 54 | 845 ppm PPA + 70% ethanol | 1.8 | 5 min | 3.75 |

Example 55 was a solution of 500 ppm PPA in water, to which 12 N hydrochloric acid had been added to achieve a pH of about 1.5.

Example 56 was a solution of 60 wt. % ethanol in water, to which 12 N hydrochloric acid had been added to achieve a pH of about 1.5.

Example 57 was a solution of 60 wt. % ethanol and 500 ppm PPA in water, to which 12 N hydrochloric acid had been added to achieve a pH of about 1.5.

Example 58 was a solution of 500 ppm PPA in water, to which 12 N hydrochloric acid had been added to achieve a pH of about 1.5.

Example 59 was a solution of 80 wt. % ethanol in water, to which 12 N hydrochloric acid had been added to achieve a pH of about 1.5.

Example 60 was a solution of 80 wt. % ethanol and 500 ppm PPA in water, to which 12 N hydrochloric acid had been added to achieve a pH of about 1.5.

Example 61 was a solution of 1000 ppm PPA in water, to which 12 N hydrochloric acid had been added to achieve a pH of about 1.5.

Example 62 was a solution of 60 wt. % ethanol in water, to which 12 N hydrochloric acid had been added to achieve a pH of about 1.5.

Example 63 was a solution of 60 wt. % ethanol and 1000 ppm PPA in water, to which 12 N hydrochloric acid had been added to achieve a pH of about 1.5.

Example 64 was a solution of 1000 ppm PPA in water, to which 12 N hydrochloric acid had been added to achieve a pH of about 1.5.

Example 65 was a solution of 80 wt. % ethanol in water, to which 12 N hydrochloric acid had been added to achieve a pH of about 1.5.

Example 66 was a solution of 80 wt. % ethanol and 1000 ppm PPA in water, to which 12 N hydrochloric acid had been added to achieve a pH of about 1.5.

Figure 5:
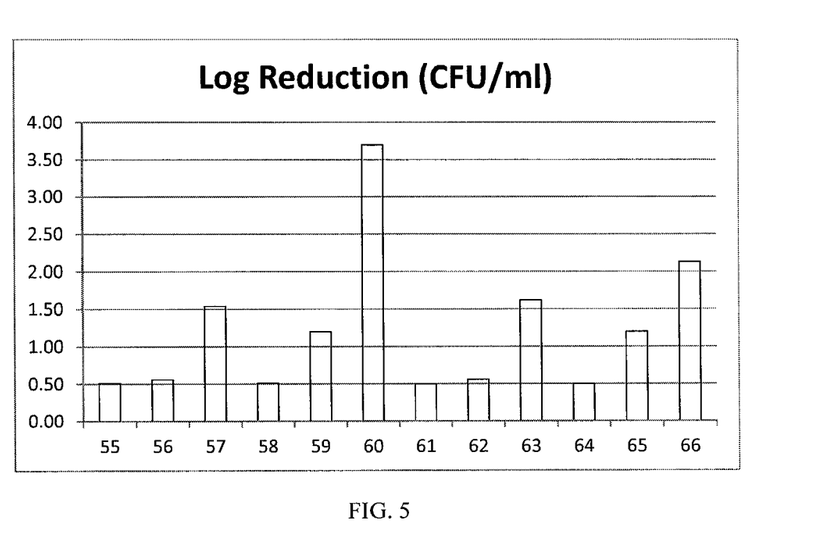
FIG. 5 is a schematic representation of the log reduction (CFU/ml) of *C. difficile* spores for various test compositions, as described herein.
Figure 6:
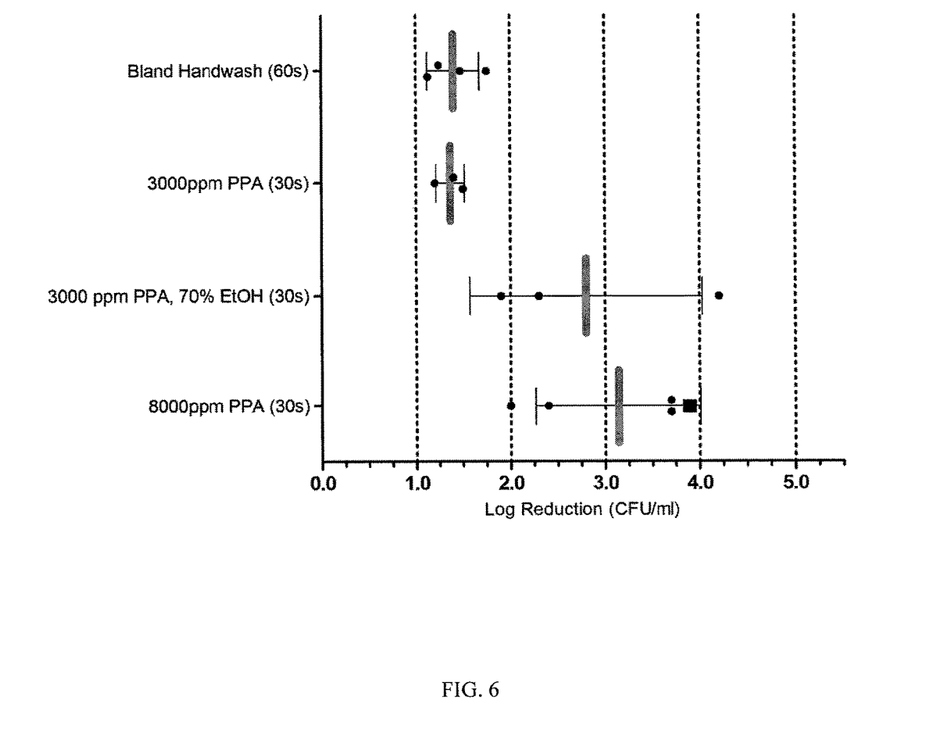
FIG. 6 is a schematic representation of the log reduction (CFU/ml) of *C. difficile* spores for various test compositions, as described herein.

As for Examples 1-18, the samples were tested for efficacy against *C. difficile* spores, according to the ASTM E 2315 method, "Standard Guide for Assessment of Antimicrobial Activity Using a Time-Kill Procedure." Contact time was 30 seconds. Results are shown in Table 4 and FIG. 5.

TABLE 4

| Example | Composition | pH | Log Reduction (CFU/ml) |
|---|---|---|---|
| 55 | 500 ppm PPA | 1.5 | 0.51 |
| 56 | 60% ethanol | 1.5 | 0.56 |
| 57 | 500 ppm PPA + 60% ethanol | 1.5 | 1.54 |
| 58 | 500 ppm PPA | 1.5 | 0.51 |
| 59 | 80% ethanol | 1.5 | 1.20 |
| 60 | 500 ppm PPA + 80% ethanol | 1.5 | 3.70 |
| 61 | 1000 ppm PPA | 1.5 | 0.50 |
| 62 | 60% ethanol | 1.5 | 0.56 |
| 63 | 1000 ppm PPA + 60% ethanol | 1.5 | 1.62 |
| 64 | 1000 ppm PPA | 1.5 | 0.50 |
| 65 | 80% ethanol | 1.5 | 1.20 |
| 66 | 1000 ppm PPA + 80% ethanol | 1.5 | 2.13 |

Example 67 was just a bland handwash, and the contact time was 60 seconds.

Example 68 was a solution of 3000 ppm PPA in water. The pH was about 2-3 and the contact time was 30 seconds.

Example 69 was a solution of 70 wt. % ethanol and 3000 ppm PPA in water, to which 12 N hydrochloric acid had been added to achieve a pH of about 1.5, and the contact time was 30 seconds.

Example 70 was a solution of 8000 ppm PPA in water, the pH was about 2-3, and the contact time was 30 seconds.

The samples were evaluated for efficacy against *C. difficile* spores according to the following in vivo test protocol. (Room temperature).

In vivo *C. difficile* Spore Test Method Protocol:
Spore Growth Media and Neutralizer
BPB+: Butterfield's Phosphate Buffer
BHIT-AMP: Brain Heart Infusion Agar with Sodium Taurocholate hydrate (0.1%) and Ampicillin (0.2 μg/ml)
Inoculum
Purified *C. difficile* spores (ATCC 700057) at an approximate concentration of 8.5 $\log_{10}$ CFU/ml. Spores were suspended in sterile water and stored at −80° C., and allowed to come to room temperature prior to testing.

Pretreatment of Hands

Pre-wash hands with bland soap (GOJO® Clear & Mild Foam Handwash) and pat dry with paper towels and wait five minutes before applying spore inoculum to hands Inoculation of Fingertips with *C. difficile* Spores Dispense 5 μL of the spore suspension directly onto the index, middle, and ring fingerpads of each hand Rub opposite fingerpads together on and off until dry Wait at least 1 minute before determining the baseline contamination of the fingers Baseline Recovery Sample one finger on each hand separately in standard size petri dishes (100×15 mm) containing 5 mL BPB+ by rubbing for one minute Pat fingerpads dry on paper towels to remove excess BPB+

Product Application

For Handwash: briefly wet hands, apply product (2 pumps of foaming hand washes), lather for 60 seconds, rinse off excess lather for 10 seconds, lightly pat dry For disinfectant compositions: (Examples): rub fingertips together under a continuous stream from a wash bottle filled with the appropriate product for the desired exposure time, briefly rinse to neutralize, lightly pat dry Post Product Exposure Recovery Sample index, middle, and ring fingers of each hand together as described above Enumeration of *C. difficile*

Dilute baseline and post product exposure recovery in BPB+ and enumerate on BHIT-AMP.

Log Reduction Calculation

After enumeration of viable *C. difficile* with subtract post exposure recovery from baselines to get a log reduction Example 71—A solution of 4000 ppm peroxypyruvic acid (PPA) in water was prepared, using distilled, deionized water. The solution was maintained in a vented container at 22° C. The concentration of PPA was monitored over time by using HPLC. After about 24 hours, the concentration of PPA had dropped to about 0, indicating that the composition was not stable over that period of time.

Various modifications and alterations that do not depart from the scope and spirit of this invention will become apparent to those skilled in the art. This invention is not to be duly limited to the illustrative embodiments set forth herein.

What is claimed is:

1. A disinfectant composition comprising:
   a first liquid pre-mix composition comprising a $C_{1-6}$ alcohol and an acidifying agent, said first liquid pre-mix composition having a pH of less than about 5; and
   a second liquid pre-mix composition that includes a diluent selected from a $C_{1-6}$ alcohol, water, and mixtures thereof, wherein said first liquid pre-mix and said second liquid pre-mix are comingled to form said disinfectant composition.

2. The composition of claim 1, wherein the disinfectant composition exhibits an enhanced efficacy against bacterial and fungal spores, when compared to the efficacy of the first liquid pre-mix composition or second liquid pre-mix composition alone.

3. The composition of claim 1, wherein the first liquid pre-mix composition comprises at least about 30 wt. % of the $C_{1-6}$ alcohol.

4. The composition of claim 1, wherein the acidifying agent is selected from the group consisting of mineral acids, organic acids, and mixtures thereof.

5. The composition of claim 1, wherein the disinfectant composition further includes at least one peracid.

6. The composition of claim 1, wherein said acidifying agent includes one or more acids having a pKa of 5.4 or less.

7. The composition of claim 1, wherein the comingled first liquid pre-mix composition and second liquid pre-mix composition have pH is from about 0.5 to about 3.

8. The composition of claim 1, wherein the $C_{1-6}$ alcohol is selected from the group consisting of methanol, ethanol, propanol, butanol, pentanol, hexanol, and isomers and mixtures thereof.

9. The composition of claim 1, wherein the $C_{1-6}$ alcohol comprises a mixture of ethanol and isopropanol.

10. The composition of claim 1, wherein the comingled first liquid pre-mix composition and second liquid pre-mix composition include less than 0.1 wt. % of auxiliary antimicrobial agents.

11. The composition of claim 1, wherein said composition provides a log reduction against *C. difficile* spores of at least about 1 in less than about 1 minute.

12. The composition of claim 1, wherein said composition provides a log reduction against *C. difficile* spores of at least about 1 in less than about 30 seconds.

* * * * *